(12) United States Patent
Sharif

(10) Patent No.: US 11,238,964 B2
(45) Date of Patent: Feb. 1, 2022

(54) EVENT TRACKING FOR ADVANCED THERAPY MEDICINAL PRODUCTS

(71) Applicant: ATMPS Ltd, London (GB)

(72) Inventor: Raja Sharif, London (GB)

(73) Assignee: ATMPS LTD, London (GB)

( * ) Notice: Subject to any disclaimer, the term of this patent is extended or adjusted under 35 U.S.C. 154(b) by 0 days.

(21) Appl. No.: 17/320,931

(22) Filed: May 14, 2021

(65) Prior Publication Data

US 2021/0272665 A1 Sep. 2, 2021

Related U.S. Application Data

(63) Continuation of application No. PCT/EP2020/058022, filed on Mar. 23, 2020.

(30) Foreign Application Priority Data

Mar. 22, 2019 (GB) ..................... 1903990

(51) Int. Cl.
G16H 20/00 (2018.01)
G16H 20/10 (2018.01)
H04L 9/32 (2006.01)

(52) U.S. Cl.
CPC ............ *G16H 20/00* (2018.01); *G16H 20/10* (2018.01); *H04L 9/3297* (2013.01); *A61M 2205/6009* (2013.01); *H04L 2209/38* (2013.01)

(58) Field of Classification Search
CPC ...... G16H 20/00; G16H 20/10; H04L 9/3297; H04L 2209/38; A61M 2205/6009
See application file for complete search history.

(56) References Cited

U.S. PATENT DOCUMENTS

2020/0151708 A1* 5/2020 Sui ..................... G06Q 20/389

FOREIGN PATENT DOCUMENTS

CN 109242067 A * 1/2019
CN 109242067 A 1/2019

OTHER PUBLICATIONS

Zhang, Jinxin et al. "Blockchain use in IoT for Privacy-Preserving Anti-Pandemic Home Quarantine." Electronics (Basel) 9.10: 1gh(16). MDPI AG. (Oct. 2020) (Year: 2020).*
International Search report and Written Opinion dated Jun. 17, 2020 for PCT International Application No. PCT/EP2020/058022.

(Continued)

*Primary Examiner* — Linh Giang Le
(74) *Attorney, Agent, or Firm* — EIP US LLP

(57) ABSTRACT

There is provided a system for tracking events associated with a treatment by personalised medicine, the system comprising a plurality of nodes hosting a blockchain. The plurality of nodes include a plurality of sequence manager nodes, each associated with a respective sequence manager contract on the blockchain, and a hub node associated with a hub contract on the blockchain. A first sequence manager contract of the sequence manager contracts is arranged to receive first event data indicating a first event associated with the treatment, and store the first event data on the blockchain in association with a first event sequence. The hub contract is arranged to store an association between the first event sequence and one or more further event sequences associated with the treatment, on the blockchain.

13 Claims, 11 Drawing Sheets

(56) References Cited

OTHER PUBLICATIONS

Srivastava et al., "Automated Remote Patient Monitoring: Data Sharing and Privacy Using Blockchain", Arxiv.org, Cornell University Library, 201 Olin Library Cornell University Ithaca, NY 14853 Oct. 30, 2018 (Oct. 30, 2018), XP080934193.
Katuwal et al., "Applications of Blockchain in Healthcare: Current Landscape & Challenges", Arxiv.org, Cornell University Library, 201 Olin Library Cornell University Ithaca, NY 14853, Dec. 6, 2018 (Dec. 6, 2018), XP080990107, paragraph [04.2].
"Quorum Whitepaper", Nov. 22, 2016, XP055496924.
"White Paper . ethereum/wiki Wiki . GitHub", Jun. 11, 2015, XP055519858 https://github.com/ethereum/wiki/wiki/White-Paper.

* cited by examiner

EVENT TRACKING FOR ADVANCED THERAPY MEDICINAL PRODUCTS

CROSS-REFERENCE TO RELATED APPLICATIONS

This application is a continuation of International Application No. PCT/EP2020/058022, filed Mar. 23, 2020 which claims priority to UK Application No. GB 1903990.8, filed Mar. 22, 2019, under 35 U.S.C. § 119(a). Each of the above-referenced patent applications is incorporated by reference in its entirety.

BACKGROUND OF THE INVENTION

Field of the Invention

The present invention relates to tracking events associated with a type of medical treatment commonly referred to as personalised medicine or advanced therapy medicinal products (ATMP), for example cell and gene therapy (CGT).

Description of the Related Technology

Advanced therapy medicinal products, encompassing personalised medicine, precision medicine and theranostics, involves tailoring of medical treatments (for example decisions, practices, interventions and/or products) to an individual patient based on the patient's predicted response to the treatment and/or the patient's predicted risk of disease. In personalised medicine, diagnostic testing is employed for selecting an optimal treatment based on a patient's genetic makeup and/or other molecular or cellular analysis. Cell and gene therapy (CGT) is a specific type of personalised medicine in which immune cells are harvested from a patient and reprogrammed to target cancer in the same patient. CGT has been found to be effective for treatment of B-cell acute lymphoblastic leukaemia, diffuse large B-cell lymphoma, and primary mediastinal B-cell lymphoma, even in cases of advanced tumours and where other treatment options have been unsuccessful.

Personalised medicine, and CGT more specifically, is highly complex, and a single treatment generally requires multiple treatment stages to be performed in sequence, usually by multiple parties. CGT, in particular, is also time-critical, such that particular stages of the treatment must be performed within specified time limits, otherwise the entire treatment sequence must be restarted. Furthermore, certain materials involved in the treatment must be kept strictly within specified temperature ranges, otherwise the entire treatment sequence must be restarted. Due to the high cost of the treatment and limited availability of resources, in some cases restarting the sequence may be impracticable, resulting in grievous consequences for a patient. Furthermore, for patients diagnosed with advanced cancers, survival may depend on the treatment being successful on the first attempt.

The above considerations necessitate a reliable system for tracking materials and processes at the various stages of a treatment by personalised medicine. The system must be absent of any single point of failure, for example caused by human error by one of the parties involved in the treatment sequence, or by failure of one or more computer systems operated by the parties.

SUMMARY

According to a first aspect of the present invention, there is provided a system for tracking events associated with a treatment by personalised medicine, the system comprising a plurality of nodes hosting a blockchain. The plurality of nodes include a plurality of sequence manager nodes, each associated with a respective sequence manager contract on the blockchain, and a hub node associated with a hub contract on the blockchain. A first sequence manager contract of the sequence manager contracts is arranged to receive first event data indicating a first event associated with the treatment, and store the first event data on the blockchain in association with a first event sequence. The hub contract is arranged to store an association between the first event sequence and one or more further event sequences associated with the treatment, on the blockchain.

According to a second aspect of the invention, there is provided a method of tracking events associated with a treatment by personalised medicine using a blockchain hosted by a plurality of sequence manager nodes each having an associated sequence manager contract on the blockchain, and a hub node having an associated hub contract on the blockchain. The method includes: receiving, by a first sequence manager contract of the sequence manager contracts, first event data indicating a first event associated with the treatment; storing, by the first sequence manager contract, the first event data on the blockchain in association with a first event sequence; and storing, by the hub contract, an association between the first event sequence and one or more further event sequences associated with the treatment, on the blockchain.

Further features and advantages of the invention will become apparent from the following description of preferred embodiments of the invention, given by way of example only, which is made with reference to the accompanying drawings.

DETAILED DESCRIPTION

Figure 1:
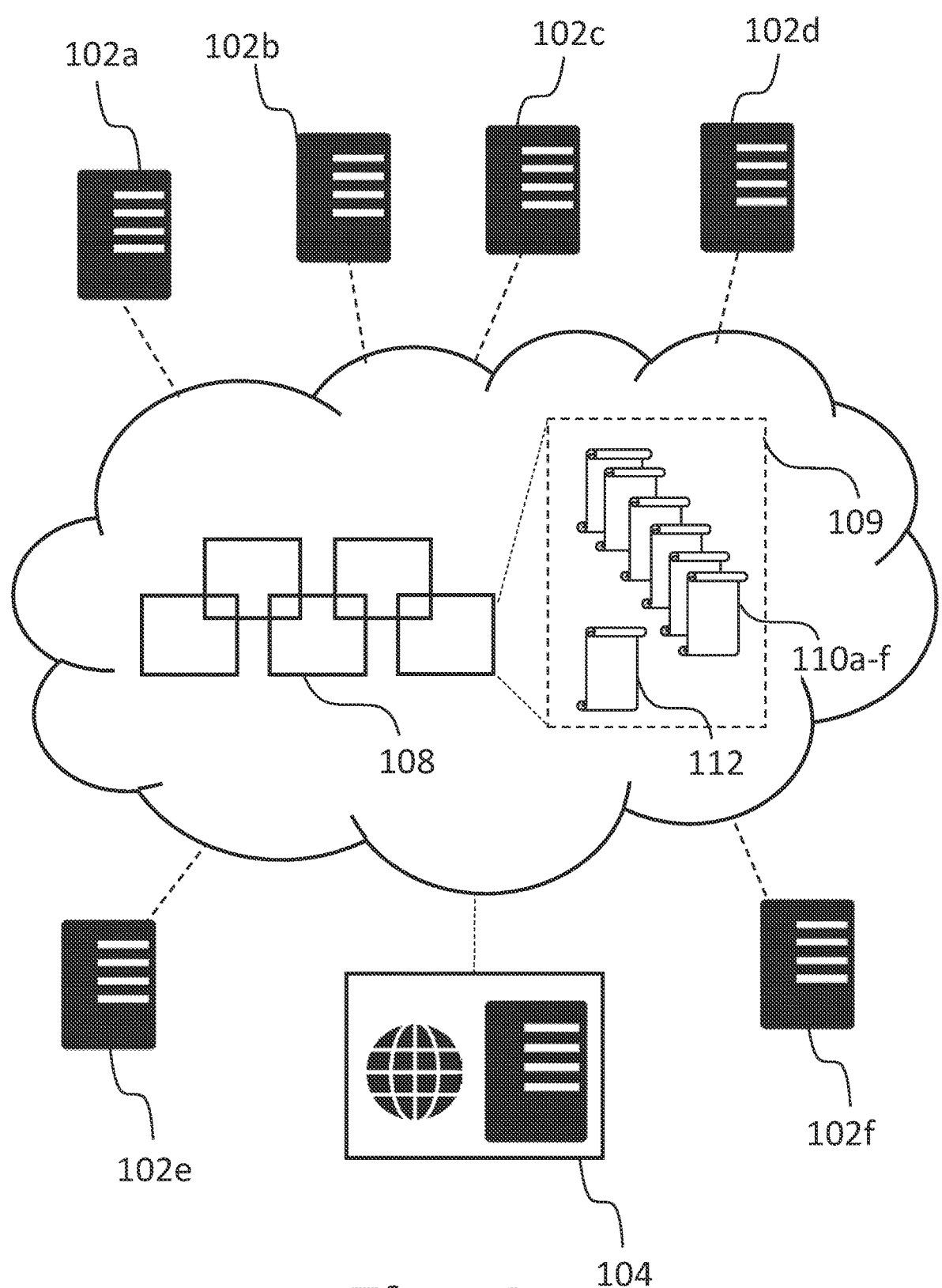
FIG. 1 shows schematically a system for tracking events associated with a treatment by cell and gene therapy.

FIG. 1 shows an example of a system 100 for tracking events associated with a treatment by cell and gene therapy.

The system includes multiple sequence manager nodes 102a-f, referred to hereafter as sequence manager nodes 102, and a hub node 104. In this example, the sequence manager nodes 102 and the hub node 104 are physical servers. In other examples, sequence manager nodes and/or a hub node may instead be implemented as network-hosted web servers. The sequence manager nodes 102 and the hub node 104 are operated by different entities involved in the administration of the treatment by cell and gene therapy. The entity operating the hub node 104 is responsible for co-ordinating the tracking of the entire treatment, and entities operating the sequence manager nodes 102 perform specific tasks related to the treatment. As the various stages of the treatment progress, custody associated with the treatment (for example, custody of physical materials associated with the treatment) and the responsibility of tracking the treatment is passed between the entities, as will be described in more detail hereafter with reference to a specific example.

The sequence manager nodes 102 and the hub node 104 are connected to a network 106, and record data associated with events during the treatment as transactions on a permissioned blockchain 108. The permissioned blockchain 108 has associated state storage 109 that stores a current state of the blockchain 108, including any smart contracts uploaded to the blockchain 108 and smart contract storage associated with those smart contracts. In this example, the permissioned blockchain 108 is based on Quorum, which is a blockchain and smart contract platform based on Ethereum. Quorum includes functionality to support private smart contracts and private transactions. Data stored in association with private smart contracts and private transactions is only accessible to specified nodes in a network. Quorum smart contracts are generally written in high-level programming languages such as Solidity, Serpent, or Lisp Like Language (LLL), and specify rules that govern transactions between accounts with addresses on the blockchain 108, as well as messages transmitted between the smart contracts themselves. Quorum is Turing complete, meaning that that in principle, Quorum smart contracts may be programmed to perform any reasonable computing task, provided that sufficient computing resources (for example, memory) are available.

When a smart contract is uploaded to the permissioned blockchain 108, the smart contract code is compiled into virtual machine code, which is executed by nodes that download and verify blocks that form the permissioned blockchain 108. The execution of the virtual machine code generally results in a change in the state of the permissioned blockchain 108. Multiple nodes (in this example, the sequence manager nodes 102 and the hub node 104) execute the same virtual machine code associated with a given block, and consensus between the downloaded blocks is ensured using a consensus algorithm such as Raft or Istanbul BFT. Consensus between the nodes builds redundancy into the system such that there is no single point of failure within the tracking system 100.

Using a permissioned blockchain allows for a significantly higher transaction throughput than the alternative option of using public blockchain such as the Ethereum main chain. The blockchain 108 only needs to store transactions and smart contracts related to the tracking system 100. By contrast, the Ethereum main chain includes transactions and smart contracts relating to a large number of entities, many of which are completely unrelated. Furthermore, data stored on the permissioned blockchain 108 is only accessible to the nodes hosting the permissioned blockchain 108 (i.e. the sequence manager nodes 102 and the hub node 104), resulting in improved data security compared with that of a public blockchain. Nevertheless, a public blockchain could be used in place of the permissioned blockchain 108.

The sequence manager nodes 102 and the hub node 104 each have an associated blockchain account with an address on the permissioned blockchain 108. An address of a blockchain account is derived from a cryptographic public key associated with the account, which in turn is derived from a cryptographic private key associated with the account. Transactions sent from a given account are signed by the associated private key, allowing a recipient of the transaction (which, generally, may be another account or a smart contract) to verify that the transaction was actually sent by that account.

Each of the sequence manager nodes 102x (where x is one of a-f) is associated with a respective sequence manager contract 110x on the permissioned blockchain 108. The sequence manager contracts 110x are instances of the same smart contract, and are referred to collectively as sequence manager contracts 110. Each sequence manager contract 110x stores a record of the blockchain address of the associated sequence manager node 102x, and is only able to accept transactions from that sequence manager node 102x, as opposed to another sequence manager node 102y (where y is not the same as x) or the hub node 104. The hub node 104 is associated with a hub contract 112 on the permissioned blockchain 108. The hub contract 112 stores a record of the blockchain address associated with the hub node 104, and is only able to accept transactions from the hub node 104 (as opposed to the sequence manager nodes 102).

Each sequence manager contract 110x has an address on the permissioned blockchain 108 and includes smart contract code and associated storage for storing event data on the permissioned blockchain 108. The sequence manager contract 110x is arranged to receive the event data from the associated sequence manager node 102x, where the event data indicates events associated with the treatment by cell and gene therapy and performed by the entity operating the associated sequence manager node 102x. The sequence manager contract 110x is, by default, private to the sequence manager node 102x and the hub node 104, such that data stored on the permissioned blockchain 108 by the sequence manager contract 110x is encrypted and cannot be viewed by other sequence manager nodes 102y. In some cases, a sequence manager contract 110x may be configured to allow one or more additional sequence manager nodes 102y to view data stored by the sequence manager contract 110x. Privacy of data relating to the treatment by cell and gene therapy is an essential requirement of the system 100. By ensuring that each party associated with the treatment may only interact with an associated sequence manager contract, data privacy between parties is ensured.

The content of the event data indicating a given event depends on an event type of the event. The sequence manager contract 110x is arranged to perform a number of processing operations in response to receiving event data from the associated sequence manager node 102x, such that the storing of the event data on the permissioned blockchain 108 is dependent on the outcome of these processing operations. The specific processing operations for storing a given event depend on the event type, as will be described in more detail hereafter. The sequence manager contract 110x stores the event data indicating a given event in association with an event sequence. An event sequence includes event data indicating events relating to a single treatment, and received from the same sequence manager node 102x. In the present example, the event data in a given event sequence indicates events performed by the entity operating the corresponding sequence manager node 102x.

The hub contract 112 has an address on the permissioned blockchain 108 and includes smart contract code and associated storage for storing, on the permissioned blockchain 108, associations between event sequences relating to a single treatment. More precisely, the hub contract 112 is arranged to store multiple segment groups, each relating to a respective treatment. Each segment group includes data indicating one or more event sequences stored by one or more respective sequence manager contracts 110. In this way, the hub contract 112 links together events relating to a single treatment but performed by multiple entities.

Figure 2:
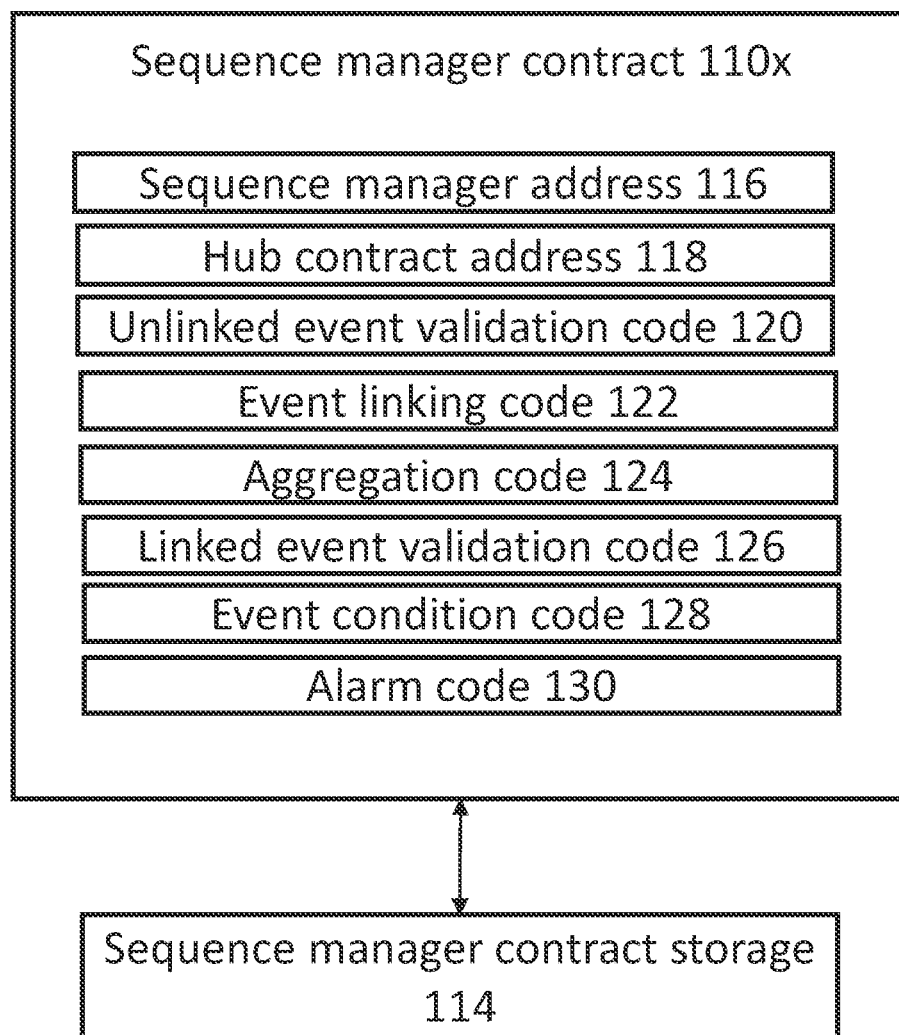
FIG. 2 is a schematic block diagram showing an example of a sequence manager smart contract utilised in the system of FIG. 1.

As shown in FIG. 2, a sequence manager contract 110x has associated sequence manager contract storage 114. In the present example, the sequence manager contract storage 114 is on-chain, meaning that it forms part of a global state of the permissioned blockchain 104, and is stored by every node that downloads and verifies an associated block in the permissioned blockchain 104. In other examples, sequence manager storage may be off-chain, meaning that it is stored independently from the permissioned blockchain 108. In either case, the sequence manager contract storage 114 is arranged such that verification of blocks of the permissioned blockchain 108 ensures immutability of data stored in the sequence manager contract storage 114. The sequence manager contract 110x can read data from the sequence manager contract storage 114 and can write data to the sequence manager contract storage 114. The sequence manager contract 110x stores a record of the blockchain address 116 of the account associated with the corresponding sequence manager node 102x. The sequence manager contract 110x only accepts transactions from the specified address 116, so only the entity that operates that sequence manager node 102x is able to upload event data to the blockchain 108 via the sequence manager contract 110x. The sequence manager contract 110x also includes the blockchain address 118 of the hub contract 112. As will be explained in more detail hereafter, the sequence manager contract 110x exchanges messages with the hub contract 112 for various reasons, including for linking event sequences together in a segment group.

The sequence manager contract 110x includes unlinked event validation code 120. This code is executed in response to the corresponding sequence manager node 102x sending event data via a transaction to the sequence manager contract 110x. The unlinked event validation code 120 validates received event data without reference to any other events in an event sequence. In the present example, the unlinked event validation includes determining that predetermined mandatory data fields are completed within the received event data. For any type of event, the predetermined mandatory data fields include a treatment identifier that is unique to an individual treatment, and an event type. Further mandatory data fields depend on the event type, and will be described in more detail hereafter with reference to a specific example. If the event data fails to satisfy the unlinked event validation, the sequence manager contract 110x will not store the event data on the permissioned blockchain 108.

The sequence manager contract 110x also includes event linking code 122. The sequence manager contract 110x executes the event linking code 122 when event data is successfully validated using the unlinked event validation code 120. If the event corresponds to a receiving of custody by the party operating the associated sequence manager node 102x (for example, in the case of a receipt of physical materials associated with a treatment), the event linking code 122 generates a new sequence in the sequence manager contract storage 114. The new sequence is allocated a new unique sequence identifier. For any event that does not correspond to a receiving of custody, the event linking code 122 searches the sequence manager contract storage 114 for an event sequence stored on the permissioned blockchain 108 with the same treatment identifier. If an event sequence with the same treatment identifier is located, the event linking code 122 adds the event data to the located event sequence. If the event linking fails, for example because an expected event sequence is not located, the sequence manager contract 110x will not store the event data on the permissioned blockchain 108.

The sequence manager contract 110x includes aggregation code 124. The aggregation code 124 is executed when the event type indicates a commissioning of physical materials, a receipt of physical materials, or a packing of physical materials. When the event type indicates a commissioning or receipt of physical materials, the aggregation code 124 stores, in association with the new event sequence generated by the event linking code 122, a new aggregation identifier. When the event type indicates a packing of physical materials, the aggregation code 124 retrieves an aggregation identifier from the existing event sequence to which the event is added, and stores aggregation data indicating that the physical materials are packed within a container. The physical materials and the container each have an identifier, and the aggregation data stores these identifiers hierarchically to indicate the packing of the physical materials within the container. At a later time, the container may be packed within a further container, in which case the aggregation code 124 adds an identifier of the further container to the hierarchical aggregation data. Alternatively, the physical materials may be unpacked from the container, in which case the aggregation code 124 removes the association between the identifiers of the physical materials and the container. The sequence manager contract 110x uses the aggregation data to check for consistency between events added to an event sequence, as will be described in more detail hereafter.

Figure 3:
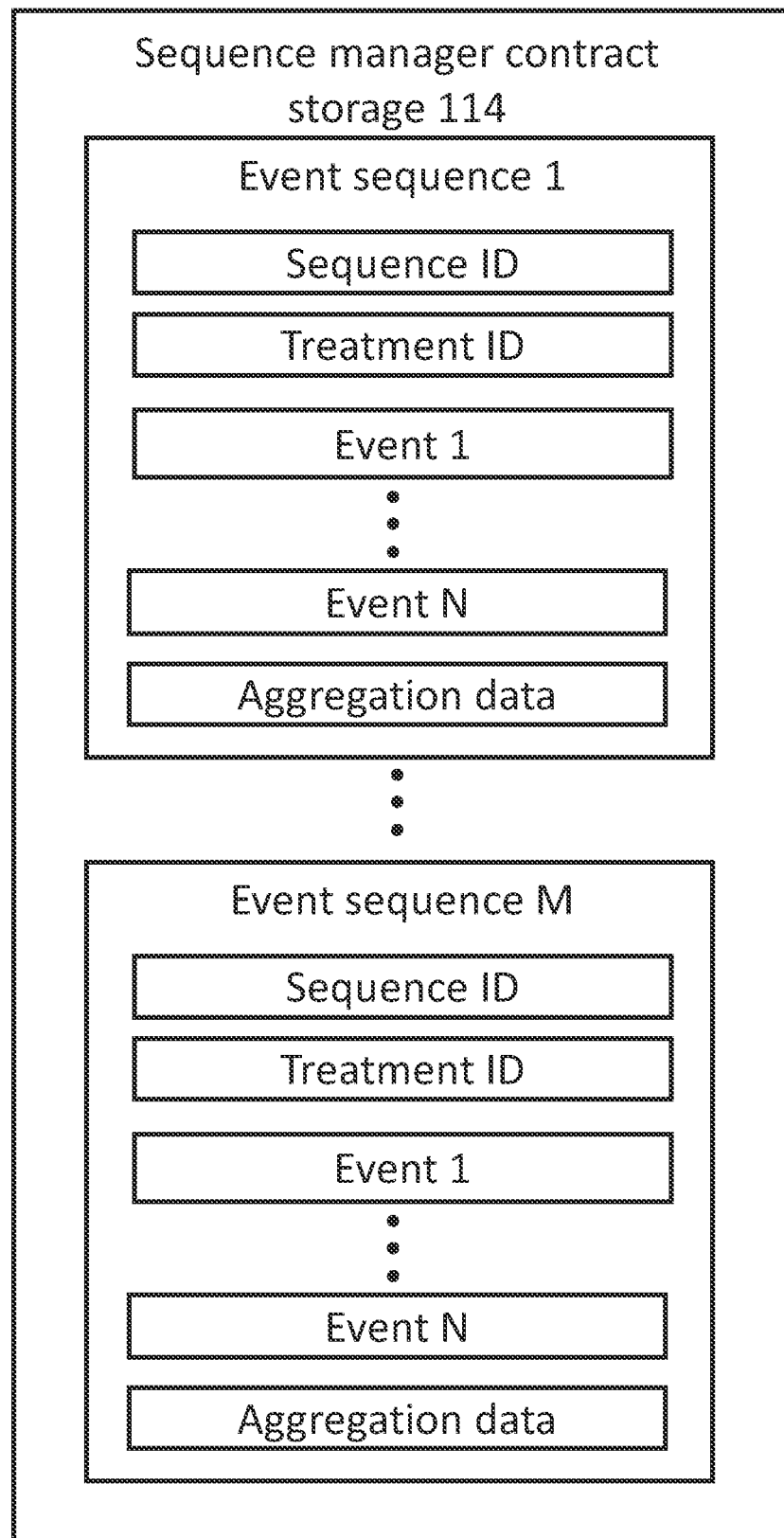
FIG. 3 is a schematic block diagram showing an example of data stored in association with a sequence manager smart contract as shown in FIG. 2.

As shown in FIG. 3, the sequence manager contract storage 114 is arranged to hold multiple event sequences. Each event sequence is allocated a sequence identifier, and is associated with a single treatment having a treatment identifier as mentioned above. The event sequence includes event data indicating events associated with that treatment, and performed by the operator of the associated sequence manager node 102. Each event sequence also includes hierarchical aggregation data indicative of any packing of physical materials associated with the treatment.

Figure 4:
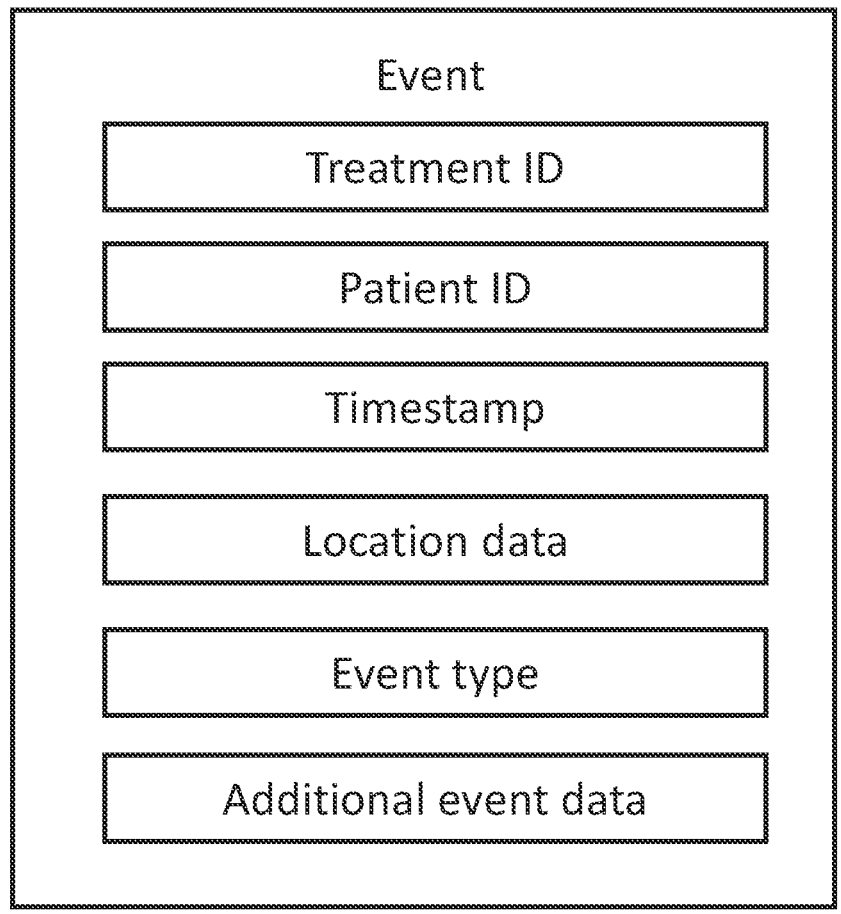
FIG. 4 is a schematic block diagram showing an example of a data structure stored in association with a sequence manager smart contract as shown in FIG. 2.

FIG. 4 shows an example of a data structure indicating an event. The data structure includes a treatment identifier to indicate which treatment the event relates to, and a patient identifier unique to the patient receiving the treatment. The treatment identifier is used by the sequence manager contract 110x to link the event to an event sequence, and is further used by the hub contract 112 to link event sequences together to form a segment group. The patient identifier is used instead of a name or any other personal information to ensure that data stored on the permissioned blockchain 108 is anonymous, and that parties performing various actions in respect of the treatment are not able to identify the patient to whom the treatment is administered. As will be described in more detail hereafter, only the party that enrolls the treatment (which, in this example is an oncologist) has a record of the association between the patient identifier and the identity of the patient. In this way, the privacy of the patient is protected.

The event data includes a timestamp indicating a time at which the event occurred, and location data indicating a location at which the event occurred (for example, longitudinal and latitudinal co-ordinates). In the present example, the timestamp and the location data are automatically determined when the event occurs, as will be described in more detail with reference to specific type of event. The event data also includes an event type, and additional event data that depends on the event type. As explained above, event data will only be successfully stored on the permissioned blockchain 108 if the event data includes mandatory event data in accordance with the event type.

Returning to FIG. 2, the sequence manager contract 110x includes linked event validation code 126. The sequence manager contract 110x executes the linked event validation code 126 after the event linking code 122 (and, if the aggregation code 124 is executed, after the aggregation code 124). In the present example, the linked event validation code 126 ensures that the event data is consistent with the events previously uploaded to the event sequence (i.e. in the correct order). If the event data fails to satisfy the linked event validation, the sequence manager contract 110x will not store the event data on the permissioned blockchain 108. If the event data indicates a receiving of custody, the event validation code 126 causes messages to be exchanged with the hub contract 112 to determine whether authorisation has been given to the sequence manager contract 110x to upload the event data, as will be described in more detail hereafter.

The sequence manager contract 110x includes event conditional code 128. The event conditional code 128 depends on the event type of the uploaded event data, and includes conditions that must be satisfied for the event to be successfully added to the event sequence. Examples of conditions associated with specific events will be described in more detail hereafter.

The sequence manager contract 110x includes alarm code 130. The alarm code 130 is executed if any of the conditions specified in the event conditional code 128 are not satisfied. The alarm code 130 causes the sequence manager contract 110x to emit an alarm event on the permissioned blockchain 108, and further to send a message to the hub contract 112, causing the hub contract 112 to emit an alarm event on the permissioned blockchain 108. As will be described in more detail hereafter, the sequence manager node 102x associated with the sequence manager contract 110x is arranged to listen for alarm events emitted by the sequence manager contract 110x, such that a user of the sequence manager node 102x can be alerted immediately if a condition specified by the event conditional code 128 is not satisfied. Similarly, the hub node 104 is arranged to listen for alarm events emitted by the hub contract 112, so that a user of the hub node 104 can be alerted immediately if a condition specified by the event conditional code is 128 not satisfied.

Figure 5:
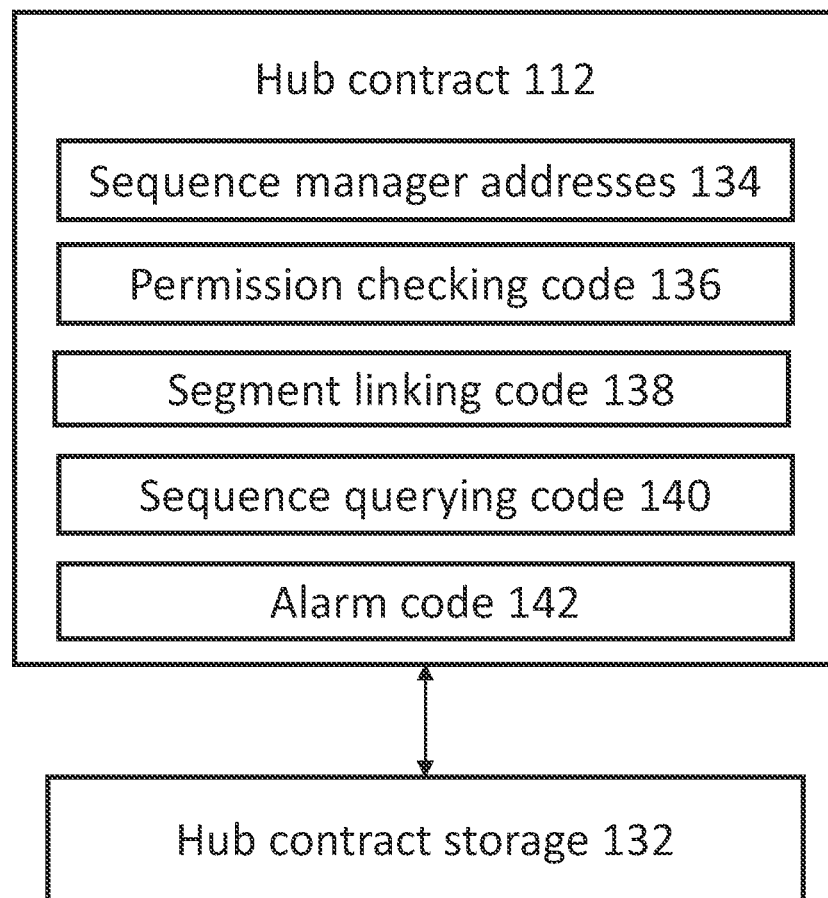
FIG. 5 is a schematic block diagram showing an example of a hub smart contract utilised in the system of FIG. 1.

As shown in FIG. 5, the hub contract 112 has associated hub contract storage 132 on the permissioned blockchain 108. In the present example, the hub contract storage 132 is on-chain. In other examples, hub contract storage may be off-chain. In either case, the hub contract storage 132 is arranged such that verification of blocks of the permissioned blockchain 108 ensures immutability of data stored in the hub contract storage 132. The hub contract 112 can read data from the hub contract storage 132 and can write data to the hub contract storage 132. The hub contract 112 stores a record of the blockchain addresses 134 of the sequence manager contracts 110. The hub contract 114 exchanges messages with the sequence manager contracts 110 to grant or deny permission for certain event data to be stored on the permissioned blockchain 108, and to link event sequences together in a segment group.

The hub contract 112 includes permission checking code 136, which is executed in response to the hub contract 112 receiving a message from a sequence manager contract 110x indicating a receiving of custody by an operator of the associated sequence manager node 102x. The message constitutes a request for permission to store corresponding event data on the permissioned blockchain 108. The message includes a sequence identifier generated by the sequence manager contract 110x as described above, and a treatment identifier for the treatment. The permission checking code 136 is arranged to determine that the sequence manager contract 110x is permitted to store the event data on the permissioned blockchain 108. In the present example, the permission checking code determines whether the sequence manager contract 110x is permitted to store the event data by querying a further sequence manager contract 110y for event data indicating that the sequence manager contract 110x is permitted to store the event data (and accordingly, indicating that the operator of the sequence manager node 102y intends to transfer custody to the operator of the sequence manager node 102x).

The hub contract 112 includes segment linking code 138, which is executed in response to the permission checking code 136 determining that the sequence manager contract 110x is permitted to store event data on the permissioned blockchain 108. The segment linking code 138 searches the hub contract storage 114 for a segment group with the same treatment identifier as the event data to be stored. If a segment group with the same treatment identifier is located, the segment linking code 138 adds the sequence to the located segment group.

Figure 6:
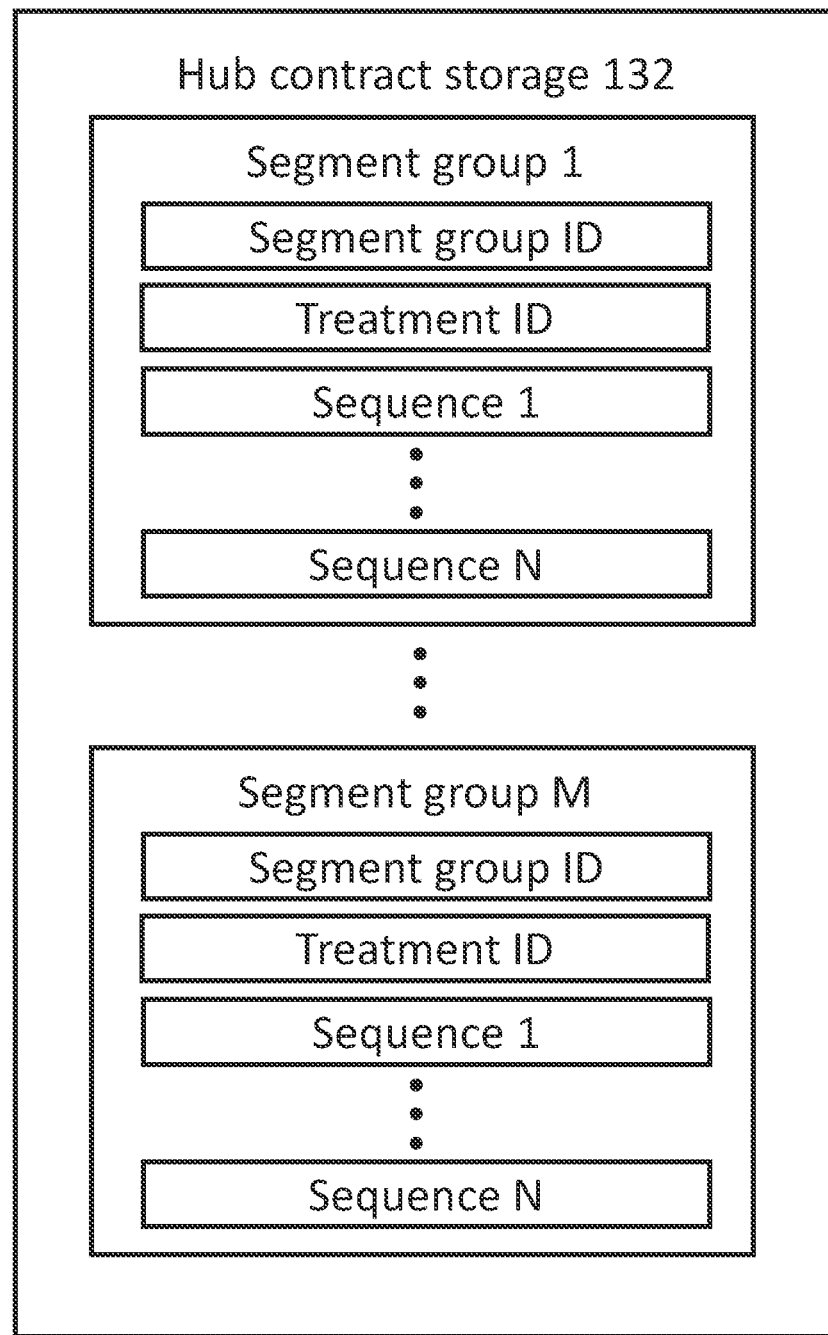
FIG. 6 is a schematic block diagram showing an example of data stored in association with a hub smart contract.

As shown in FIG. 6, the hub contract storage 132 is arranged to hold multiple segment groups. Each segment group is allocated a segment group identifier, and is associated with a single treatment having a treatment identifier as mentioned above. The segment group includes data indicative of the sequences relating to that treatment, including the sequence identifier for each sequence, and data indicative of the sequence manager contract 110x responsible for the sequence (for example, the address of the sequence manager contract 110x on the permissioned blockchain 108.

Returning to FIG. 5, the hub contract 112 includes sequence querying code 140. The sequence querying code 140 is executed in response to the hub contract 112 receiving a query from the hub node 104 regarding event data within sequences in a given segment group. The sequence querying code 140 is also executed in response to the hub contract 112 receiving a message from one of the sequence manager contracts 110 requesting permission relating to a receipt of custody associated with a treatment. The sequence querying code 140 causes the hub contract 112 to send a message to a sequence manager contract 110x to request event data stored by that sequence manager contract 110x.

The hub contract 112 includes alarm code 142. The alarm code 142 is executed in response to the hub contract 112 receiving an alarm message from one of the sequence manager contracts 110 indicating that one or more event conditions is not satisfied. The alarm code 142 causes the hub contract 112 to emit an alarm event on the permissioned blockchain 108. The hub node 104 is arranged to listen for alarm events emitted by the hub contract 112, so that a user of the hub node 104 can be alerted immediately when the one or more event conditions is not satisfied.

Figure 7:
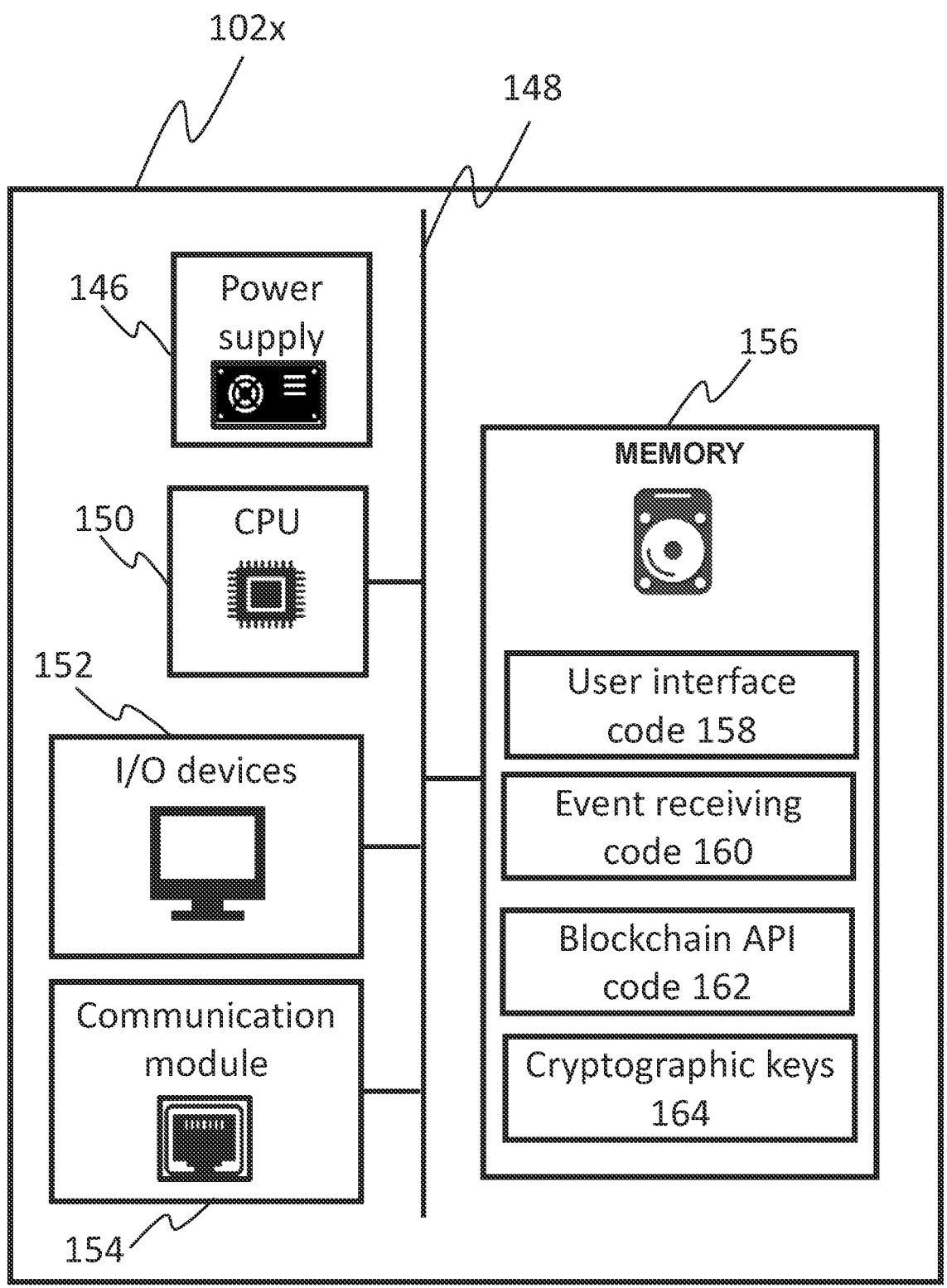
FIG. 7 is a schematic block diagram showing an example of a sequence manager node of the system shown in FIG. 1.

As shown in FIG. 7, a sequence manager node 102x includes a power supply 146 and a system bus 148. The system bus 148 is connected to: a CPU 150; input/output devices 152; a communication module 154; and memory 156. The input/output devices 152 allow a user to interact with the sequence manager node 102x, and include, for example, a keyboard, a monitor, and a mouse/trackpad. The memory 156 includes non-volatile storage and volatile memory, and holds: user interface code 158; event receiving code 160; blockchain application programming interface (API) code 162; and cryptographic keys 164.

The event receiving code 156 is executed when new event data is uploaded to the sequence manager node 102x. For some events, event data is input manually by a user via a user interface of the sequence manager node 102x. For other events, event data is generated automatically and/or received via the communication module 154. One example in which event data is generated automatically uploaded is where the event data corresponds to a measurement by an automatic temperature sensor of a temperature of physical materials associated with the treatment, in which case the automatic temperature sensor is arranged to transmit the measured temperature to the sequence manager node, along with further mandatory data such as the time and location of the temperature measurement. Another example in which event data is generated automatically uploaded is where physical materials are scanned using a scanning device (for example, a Quick Response (QR) code scanning device or a Near Field Communication (NFC) device) to determine an identifier associated with the physical materials.

The blockchain API code 162 allows the sequence manager node 102x to interact with the permissioned blockchain 108. The blockchain API code 162 makes is arranged to send transactions to the sequence manager contract 110x, and to query the sequence manager contract 110x for data on request of a user. In the present example, the blockchain API code 162 is also arranged to listen for alarm events emitted by the sequence manager contract 110, where the alarm events may indicate that conditions specified within the event conditional code 128 have not been satisfied by a given event submitted to the sequence manager contract 110x.

The cryptographic keys 164 include a public key and private key associated with the account of the sequence manager node 102x on the permissioned blockchain 108. The sequence manager node 102x uses this private key to sign transactions, such as the uploading of event data to the sequence manager contract 110x on the permissioned blockchain 108. The cryptographic keys 164 also include public and private keys for implementing the privacy of the sequence manager contract 110x (as mentioned earlier, the sequence manager contract 110x is private to the sequence manager node 102x and the hub node 108). In an alternative implementation, private and public keys associated with an account may also be used for implementing privacy of a contract.

Figure 8:
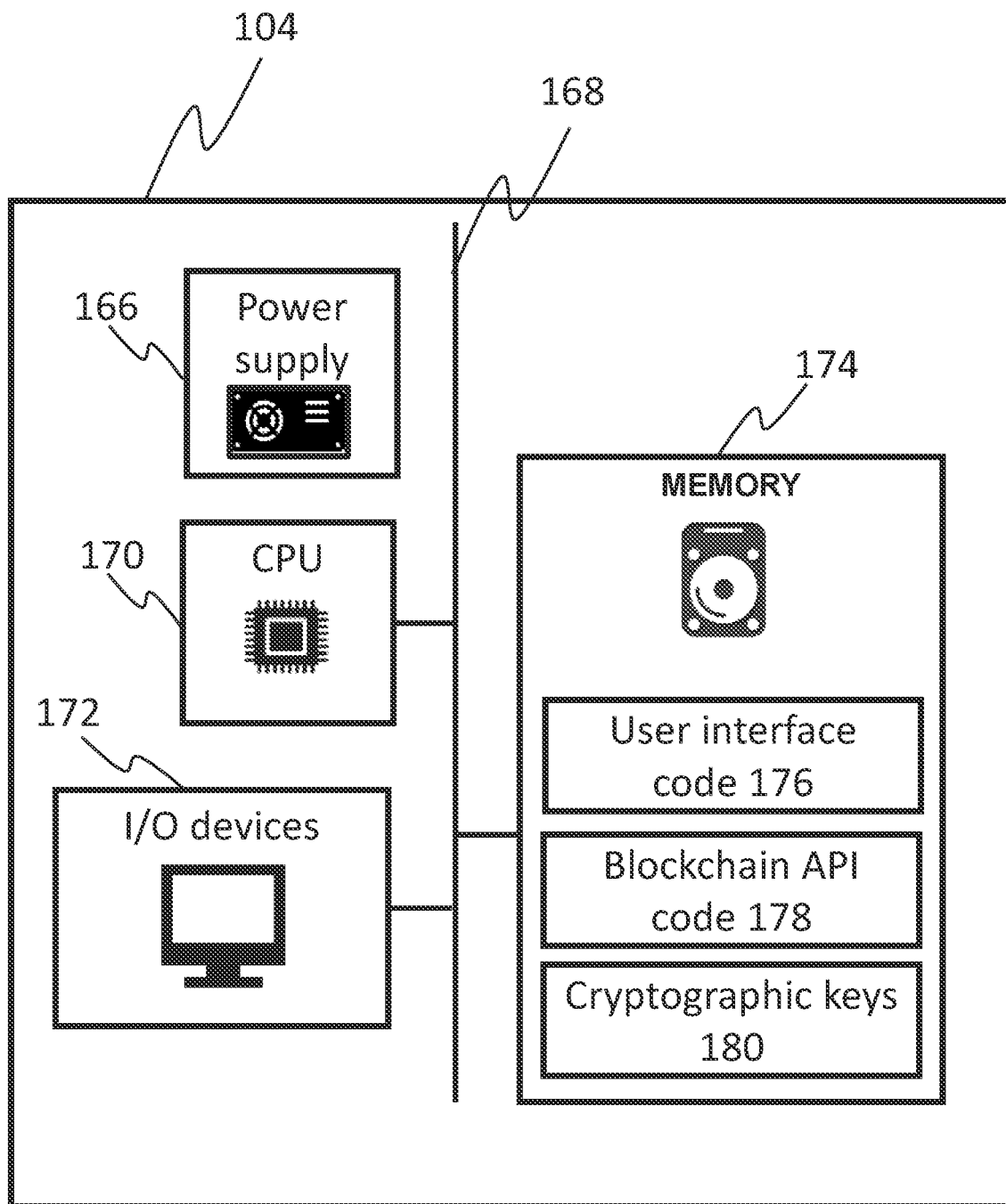
FIG. 8 is a schematic block diagram showing an example of a hub node of the system shown in FIG. 1.

As shown in FIG. 8, the hub node 104 includes a power supply 166 and a system bus 168. The system bus 168 is connected to: a CPU 170; input/output devices 172; and a memory 174. The input/output devices 172 allow a user to interact with the hub node 104, and include, for example, a keyboard, a monitor, and a mouse/trackpad. The memory 174 holds: user interface code 176; blockchain API code 178; and cryptographic keys 180.

The blockchain API code 178 allows the hub node 104 to interact with the permissioned blockchain 108. The blockchain API code 178 is arranged to hub contract 112 for data on request of a user. In the present example, the blockchain API code 178 is also arranged to listen for alarm events emitted by the hub contract 112.

The cryptographic keys 180 include a public key and private key associated with the account of the hub node 102x on the permissioned blockchain 108. The cryptographic keys 164 also include public and private keys for implementing the privacy of the hub contract 112 and the sequence manager contracts 110 (the hub contract 112 is private to the hub node 104, and the hub node 104 may also access data stored by the sequence manager contracts 110).

Figure 9:
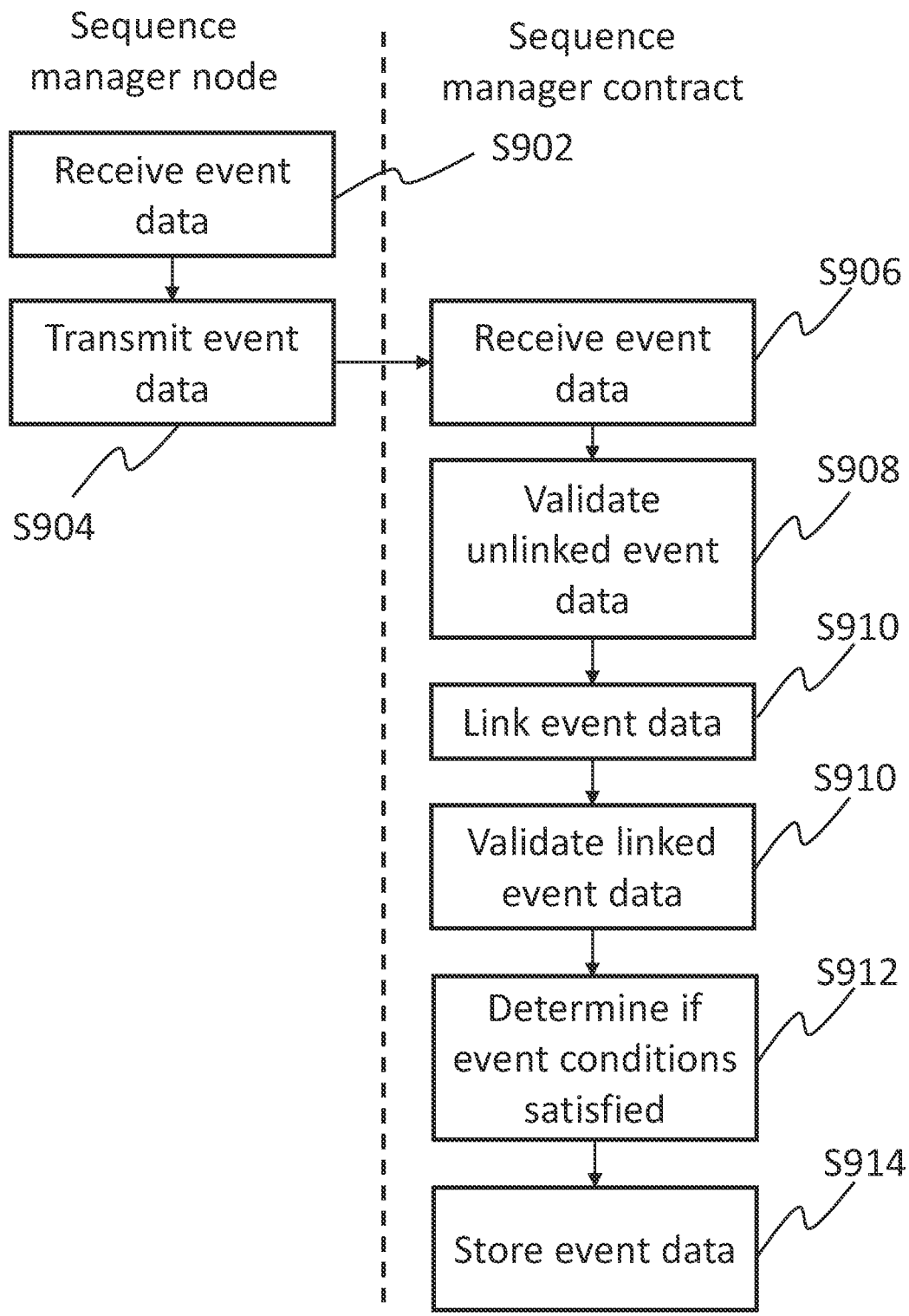
FIG. 9 is a flow diagram representing a method for storing event data associated with a treatment by cell and gene therapy on a permissioned blockchain.

FIG. 9 shows an example in which a sequence manager node 102x receives event data indicating an event associated with a treatment by cell and gene therapy. In this example, the event does not relate to a receiving of custody from a different entity. The sequence manager node 102x receives the event data at S902, either as a result of a user entering the event data via a user interface of the sequence manager node 102x, or via a signal from a sensor device or scanning device. The sequence manager node 102x transmits, at S904, the event data to the sequence manager contract 110x via a blockchain API.

The sequence manager contract 110x receives the event data at S906, and performs unlinked event validation at S908. The unlinked event validation includes ensuring that the event data includes predetermined mandatory data. The predetermined mandatory data includes a patient identifier, a treatment identifier, and an event type. Further mandatory data depends on the event type. If the unlinked event validation is unsuccessful, the sequence manager contract 110x does not store the event data on the permissioned blockchain 108.

If the unlinked event validation is successful, the sequence manager contract 110x links the event data at S910. In this example, the event type does not indicate a receiving of custody, and therefore to link the event data the sequence manager contract 110x searches the associated sequence manager contract storage 114 for a sequence identifier stored in association with the same treatment identifier as that of the event data to be linked. If no such sequence identifier is located, the event data will not be stored on the permissioned blockchain 108. If a sequence identifier is located, the sequence manager contract 110x adds the event data to the located event sequence.

If the event linking is successful, the sequence manager contract 110x performs linked event validation at S912. The linked event validation includes ensuring that the event type of the event data to be uploaded is consistent with the events previously uploaded to the event sequence if the linked event validation is successful, the sequence manager contract 110x does not store the event data on the permissioned blockchain 108.

If the linked event validation is successful, the sequence manager contract 110x determines, at S914, whether the event data satisfies event conditions depending on the event type of the event data to be stored. If any of the event conditions are not satisfied, the sequence manager contract 110x emits an alarm event on the permissioned blockchain 108, and sends an alarm message to the hub contract 104. In this way, the operator of the sequence manager node 102x and the operator of the hub node 104 are immediately notified that there is a problem. The sequence manager contract 110a stores the event data at S916.

Figure 10:
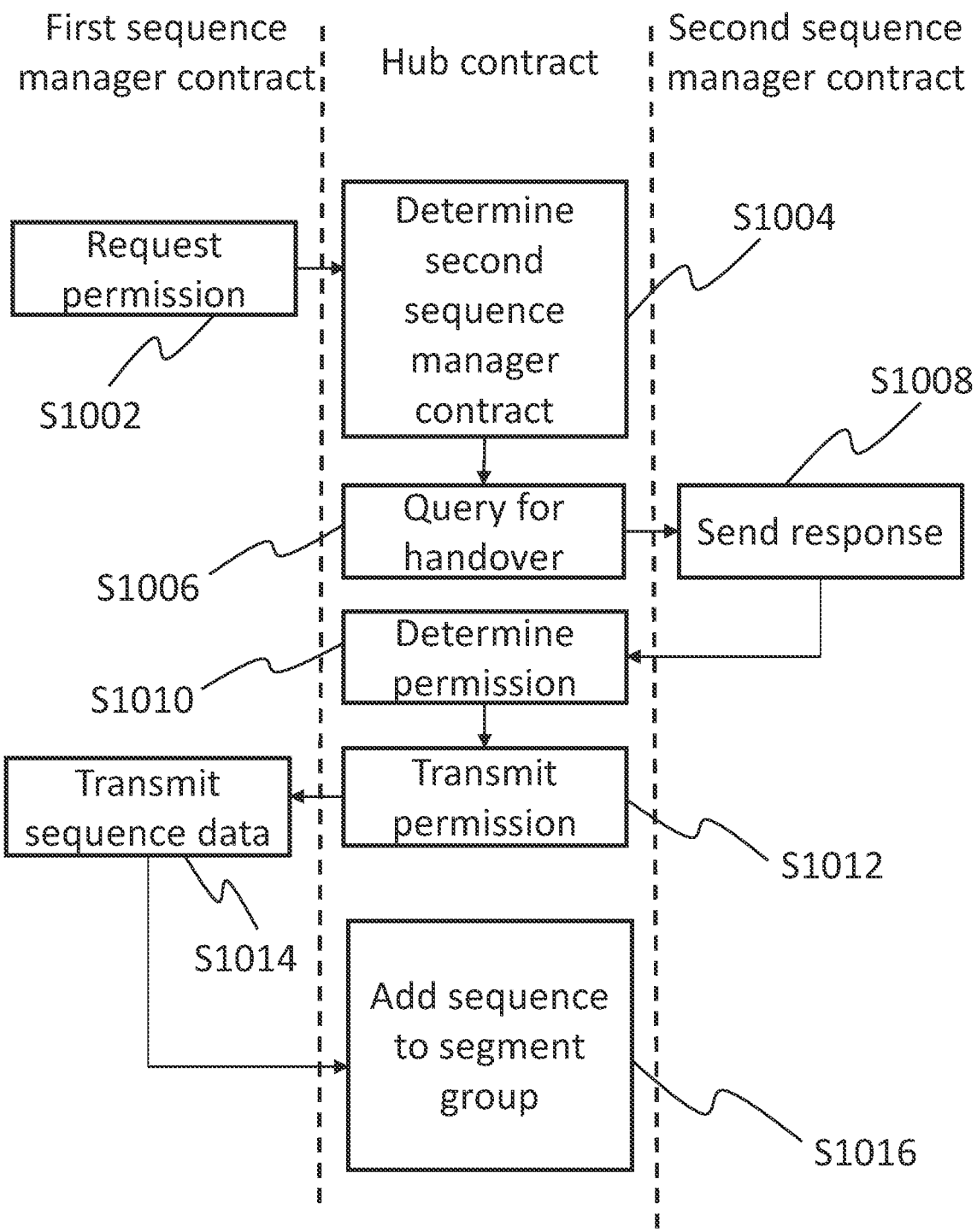
FIG. 10 is a flow diagram representing a method for storing event data indicating a receipt of physical materials relating to a treatment by cell and gene therapy on a permissioned blockchain.

FIG. 10 shows an example in which linked event validation is performed for event data relating to a receiving of custody from a different entity. The first sequence manager 110x sends, at S1002, a message to the hub contract 112 to request permission from the hub contract 112 to store the event data. The message includes the treatment identifier of the treatment to which the event data relates. Upon receiving the message, the hub contract 112 determines, at S1004, an address of a second sequence manager contract 110y on the permissioned blockchain 108. In the present example, the hub contract 112 determines the address of the second sequence manager contract 110y by searching the hub contract storage 132 for a segment group associated with the same treatment identifier as the event data to be stored, and determining the sequence manager contract 110x responsible for the most recent sequence in the segment group. In other examples, a hub contract may determine the address of the second sequence manager contract 110y in dependence on the address of first sequence manager contract 110x.

Having determined the address of the second sequence manager contract 110y, the hub contract 112 queries, at S1006, the second sequence manager contract 110y for event data indicating a passing of custody associated with the treatment, and indicating that the operator of the first sequence manager contract 110x is an intended recipient of the custody. The second sequence manager contract 110y sends, at S1008, a response to the query from the hub contract 112, indicating whether event data stored by the second sequence manager contract 110y indicates a passing of custody associated with the treatment, and that operator of the first sequence manager node 102x is an intended recipient of the custody (for example, by specifying, in an intended recipient field, an identifier associated with the operator of the first sequence manager node 102x, or the blockchain address of the first sequence manager contract 110x).

The hub contract 112 determines, at S1010, whether the first sequence manager contract 110x is permitted to store the event data indicating the receiving of custody. The first sequence manager contract 110x is permitted to store the event data if the second sequence manager contract 110y stores event data indicating the first sequence manager contract 110x as an intended recipient of a passing of custody. In other examples, a second sequence manager contract may determine whether a first sequence manager contract is permitted to store event data, in which case the second sequence manager contract sends the outcome of the determination to the hub contract 112. If the hub contract 112 determines that the first sequence manager contract 110x is not permitted to store the event data, the hub contract emits an alarm event on the permissioned blockchain 108, so that the entity overseeing the treatment is made aware that an error may have occurred.

The hub contract 112 sends, at S1012, a message to the first sequence manager contract 110x indicating the outcome of the determination. If the message indicates that the first sequence manager contract 110x is not permitted to store the event data, the first sequence manager contract 110x does not store the event data on the permissioned blockchain 108. If the message indicates that the first sequence manager contract 110x is permitted to store the event data, the first sequence manager contract 110x transmits, at S1014, sequence data to the hub contract 112. In the present example, the sequence data includes a sequence identifier associated with the sequence in which the event data will be stored. The first sequence manager contract generates the sequence identifier is generated during an event linking process, as described above. The hub contract 112 adds, at S1016, the sequence in which the event data will be stored to the segment group corresponding to the treatment.

Figure 11:
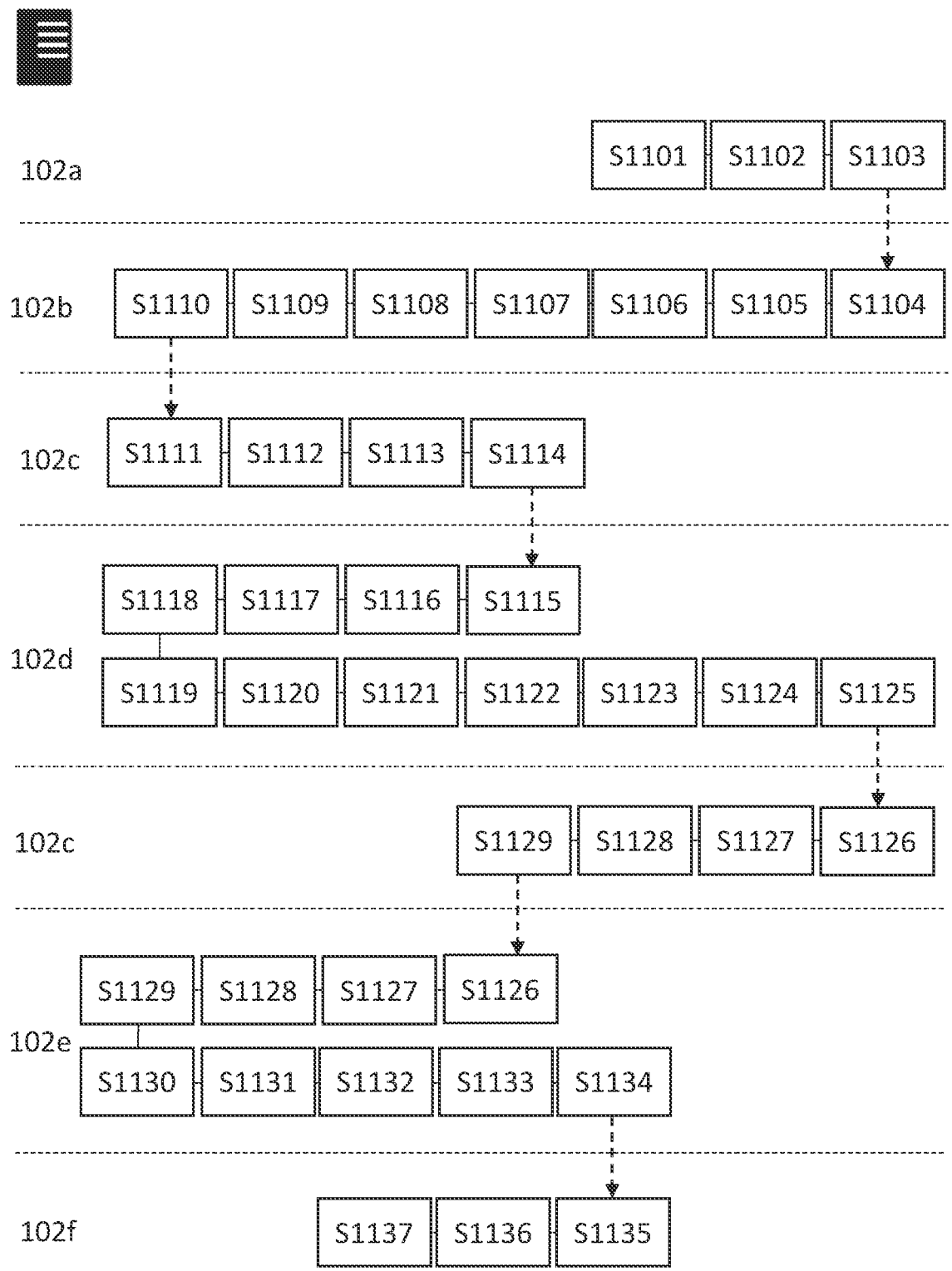
FIG. 11 shows an example of events associated with a single CGT treatment.

FIG. 11 shows an example of a sequence of events associated with a CGT treatment. The events are uploaded to the sequence manager nodes 102a-f and relate to tasks performed by the entities operating the sequence manager nodes. The dashed arrows in FIG. 11 represent transfers of custody between the entities. Details of the events are given below:

Treatment Enrolment—Performed at an Oncologist Surgery
    S1101: Select and Request Treatment
        Includes generating a unique treatment identifier and a patient identifier.
    S1102: Patient Registration
        Mandatory event data includes a hash of a completed patient registration form.
    S1103: Scheduling of Appointments
        Mandatory data includes a schedule date and a clinic identifier for treatment centre.
        Includes passing custody to a treatment centre.

Tissue Harvesting—Performed at a Treatment Centre
    S1104: Regulatory Form Attestation
        Mandatory event data includes a hash of a completed regulatory form.
        Includes checking for permission to receive custody.
    S1105: Selection Kit Commissioning
        Mandatory data includes a selection kit identifier.
        Includes generating a new aggregation identifier.
    S1106: Collection Kit Inspection
        Event conditions include pass/fail of inspection.
    S1107: Cell-Tissue Harvesting
        Event data is rejected if collection kit inspection failed.
    S1108: Cryo-Preserve
        Mandatory data includes starting temperature and ending temperature.
        Event conditions include starting temperature and ending temperature being within respective predetermined ranges, and time since last step being within a predetermined range.
        Includes time excursion check.
    S1109: Aggregate (Bag—Cryo Port)
        Includes storing aggregation data, temperature excursion check, time excursion check.
    S1110 Aggregate (Cryo Port—Shipping Container)
        Includes storing aggregation data, temperature excursion check, time excursion check, passing custody to logistics company.

Logistics—Performed by a Logistics Company
    S1111: Pick Up
        Includes checking for permission to receive custody, temperature excursion check, time excursion check.
    S1112: (Ongoing) Cold-Chain Status Check
        Temperature measured at predetermined times (e.g. periodically) by automatic temperature sensor.
        Includes temperature excursion check, time excursion check.
    S1113: Transport and Customs Clearance
        Includes temperature excursion check, time excursion check.
        Event conditions include pass/fail of clearance.
    S1114: Delivery
        Includes temperature excursion check, time excursion check, passing custody to pharmaceutical company.

Tissue Processing (CGT Activation)—Performed by a Pharmaceutical Company

S1115: Cell/Tissue Product Receiving
Includes checking for permission to receive custody, temperature excursion check, time excursion check.
S1116: Unpacking
Includes temperature excursion check, time excursion check, aggregation data check.
S1117: Cryo-Thaw
Includes temperature excursion check, time excursion check.
S1118: Cell/Tissue Product Processing
Includes temperature excursion check, time excursion check.
S1119: Cell/Tissue Product Release
Includes temperature excursion check, time excursion check
S1120: Storage
Includes temperature excursion check, time excursion check.
S1121: Quality Assurance
Includes temperature excursion check, time excursion check.
Event conditions include pass/fail of quality test.
S1122: Cryo Preservation.
Event data is rejected if collection kit inspection failed.
Mandatory data includes starting temperature and ending temperature.
Event conditions include starting temperature and ending temperature being within respective predetermined ranges, and time since last step being within a predetermined range.
S1123: Aggregate (Bag)
Includes temperature excursion check, time excursion check.
S1124: Aggregate (Bag—Cryo Port)
Includes temperature excursion check, time excursion check.
S1125: Aggregate (Cryo Port—Container)
Includes temperature excursion check, time excursion check, passing custody to logistics company.
Logistics—Performed by a Logistics Company
S1126: Pick Up
Includes checking for permission to receive custody, temperature excursion check, time excursion check.
S1127: (Ongoing) Cold-Chain Status Check
Temperature measured at predetermined times (e.g. periodically) by automatic temperature sensor.
Includes temperature excursion check, time excursion check.
S1128: Transport and Customs Clearance
Includes temperature excursion check, time excursion check.
Event conditions include pass/fail of clearance.
S1129: Delivery
Includes temperature excursion check, time excursion check, passing custody to treatment centre.
Administer Treatment—Performed at a Treatment Centre
S1130: Cell/Tissue Product Receiving
Includes checking for permission to receive custody, temperature excursion check, time excursion check.
S1131: Unpacking
Includes temperature excursion check, time excursion check, aggregation data check.
S1132: Cryo-Thaw
Includes temperature excursion check, time excursion check.
S1133: Administration to Patient
S1134: Patient Aftercare
Includes passing custody to treatment follow-up centre.
Treatment Follow-Up—Performed at Treatment Follow-Up Centre
S1135: Check-Up
Includes checking for permission to receive custody
S1136: Update to Pharmaceutical Company
S1137: Destroy Back-Up Samples A time excursion check involves determining a difference between a timestamp associated with an event and a timestamp associated with an earlier event. Depending on the event type, the earlier event may be the most recent event, or may be a predetermined earlier event. In some cases, the earlier event is stored by the same sequence manager contract 110$x$ as the later event. In other cases, the earlier event is stored by a different sequence manager contract 110$y$. If the earlier event is stored by a different sequence manager contract 110$y$, the sequence manager contract queries the hub contract 112, which queries the sequence manager contract 110$y$ for the earlier timestamp. The sequence manager contract 110$x$ receiving the later event data is arranged to emit an alarm event on the permissioned blockchain 108, and to transmit an alarm message to the hub contract, when the difference between the timestamps exceeds a threshold duration of time.

A temperature excursion check involves a temperature sensor (for example, an automatic temperature sensor) measuring a temperature of physical materials (for example, a cell/tissue product) and transmitting the measured temperature to the sequence manager node associated 102$x$ as part of the event data to be uploaded. The sequence manager contract 110$x$ is arranged to emit an alarm event on the permissioned blockchain 108, and to transmit an alarm message to the hub contract 112, when the measured temperature lies outside a predetermined range.

In the scheduling of appointments at step S1103, the sequence manager node associated with the oncologist surgery or the like may use an API to access scheduling information from the pharmaceutical company. In this way, the oncologist surgery can reserve time at the pharmaceutical company for various operations involved in the treatment processing.

As mentioned above, physical materials may be associated with a unique QR code that is scanned each time there is a handover in the change of custody. This QR code will store the unique patient identifier.

During tissue harvesting, a unique Sample_QR code is generated and a printable label including the unique Sample_QR code is generated and printed copies pf the Sample_QR code are attached to packaging associated with the harvested tissue. For example, a printed Sample_QR code may be attached to a test tube holding the harvested tissue and also on the outside of a delivery box. If a replacement tissue sample is needed, then a new Sample_QR code is issued. To highlight that this is a different sample, a visible indication may be included on the printed QR label. For example, the numbering "02" may be added.

During tissue processing, a Treatment_QR code is generated and printed copies of the Treatment_QR code are attached to packaging associated with the treatment product. Again, a printed Treatment_QR code may be attached to a test tube holding the treatment product and also on the outside of a delivery box.

Finally, to assist in tracking the chain of custody, a unique Person_QR code is associated with each person in the chain of custody, for example for a nurse at the at an oncologist surgery, a courier working for a courier firm and a lab technician working at the pharmaceutical company. These QR codes are printed and scanned during the change of custody. For example, a courier picking up a tissue sample scans both the Sample_QR code for the sample and the Person_QR code for the nurse handing over the sample, while that nurse scans the Sample_QR code for the sample and the Person_QR code for the courier. Similar operations occur each time that the tissue sample changes custody and the treatment product changes custody.

Given that there are three different types of QR code, in an example each type of QR code is printed in a given colour to avoid confusion. For example, a Sample_QR code may be printed in blue, a Treatment_QR code may be printed in Green and a Person_QR code may be printed in Black.

Example embodiments may make use of mobile applications on smartphones, tablets and the like to assist with the collation of event data. For example, the mobile application may control the scanning of QR codes during a change of custody. It will be appreciated that the mobile applications may be customised for the role of the stakeholder so that, for example, the mobile application for a courier only handles events associated with the courier.

While using QR codes is convenient, ti will be appreciated that other tagging technologies could be used such as RFID codes, NFC chips or Internet of Things (IoT) devices.

The above embodiments are to be understood as illustrative examples of the invention. Further embodiments of the invention are envisaged. For example, a system in accordance with the present invention may be used to track events relating to a different type of therapy, for example a homologous or allogenic cell and gene therapy, stem cell therapy or another form of treatment by personalised medicine. Similarly, in other embodiments the invention can be applied to blood and organ transplant. In some examples, one of the entities involved in certain stages of administering the treatment may also be responsible for overseeing the treatment (for example, an entity that enrolls a patient for the treatment). In this case, a hub node may be combined with a sequence manager node, and/or a hub contract may be combined with a sequence manager contract. In some examples, data stored on a permissioned blockchain may be anchored onto a public blockchain, such as the Ethereum main chain, for improved security.

Although the illustrated embodiments utilise Quorum, it will be appreciated that the invention is blockchain agnostic and other blockchain platforms could be used, for example the R3 Cardano, IBM Hyperledger or Oracle blockchain platforms. While there are advantages to using a permissioned blockchain as discussed above, the invention could be implemented on a public blockchain.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A system for tracking events associated with a treatment by personalised medicine, the system comprising:
   a plurality of computers and servers hosting a blockchain, the blockchain having:
   an associated state storage; and
   an updateable sequence of blocks,
   wherein the blockchain has a state of the blockchain that is stored on the associated state storage and the updateable sequence of blocks is used in verifying changes to the state of the blockchain,
   the plurality of computers and servers comprising:
   a plurality of sequence manager nodes each associated with a respective sequence manager contract forming part of the state of the blockchain, each sequence manager contract having associated sequence manager contract storage; and
   a hub node associated with a hub contract forming part of the state of the blockchain, the hub contract having associated hub contract storage,
   wherein:
   the first sequence manager node is arranged to transmit first event data to a first sequence manager contract associated with the first sequence manager node, the first event data indicating a receiving of custody associated with the treatment;
   the first sequence manager contract is arranged to:
   store the first event data on the blockchain in association with a first event sequence in a manner to change the state of the blockchain; and
   transmit first sequence data to the hub contract, the first sequence data identifying the first event sequence; and
   responsive to receiving the first sequence data from the first sequence manager contract, the hub contract is arranged to store, in the hub contract storage, association data indicating an association between the first event sequence and one or more further event sequences associated with the treatment in a manner to change the state of the blockchain; and
   the first event data and the association data are verifiable using the updateable sequence of blocks.

2. The system of claim 1, wherein:
   the first sequence manager contract is arranged to request permission from the hub contract to store the first event data on the blockchain; and
   the hub manager is arranged to determine, in response to receiving the request for permission, that the first sequence manager contract is permitted to store the first event data on the blockchain.

3. The system of claim 2, wherein the determining that the first sequence manager contract is permitted to store the first event data comprises querying a second sequence manager contract of the sequence manager contracts for second event data indicating a passing of custody associated with the receiving of custody, the second event data indicating that the first sequence manager contract is permitted to store the first event data.

4. The system of claim 1, wherein:
   the first event data indicates a packing of physical materials associated with the treatment into a container; and
   the first sequence manager contract is arranged to store aggregation data on the blockchain in association with the first event sequence, the aggregation data comprising an identifier for the physical materials and an identifier for the container.

5. The system of claim 1, wherein:
   the first event data comprises an identifier for physical materials associated with the treatment; and
   the storing of the first event data on the blockchain is dependent on the first sequence manager contract determining that the identifier is consistent with aggregation data stored in association with the first event sequence.

6. A system for tracking events associated with a treatment by personalised medicine, the system comprising:

a plurality of computers and servers hosting a blockchain, the blockchain having:
an associated state storage; and
an updateable sequence of blocks,
wherein the blockchain has a state of the blockchain that is stored on the associated state storage and the updateable sequence of blocks is used in verifying changes to the state of the blockchain,
a plurality of sequence manager nodes each associated with a respective sequence manager contract forming part of the state of the blockchain, each sequence manager contract having associated sequence manager contract storage; and
a hub node associated with a hub contract forming part of the state of the blockchain, the hub contract having associated hub contract storage,
wherein:
the first sequence manager node is arranged to transmit first event data to a first sequence manager contract associated with the first sequence manager node, the first event data indicating a first event associated with the treatment;
the first sequence manager contract is arranged to:
determine whether predetermined mandatory fields are completed within the first event data, the predetermined mandatory fields depending on an event type of the first event; and
in the event that the predetermined mandatory fields are determined to be completed within the first event data, store the first event data on the blockchain in association with a first event sequence in a manner to change the state of the blockchain;
the hub contract is arranged to store, in the hub contract storage, association data indicating an association between the first event sequence and one or more further event sequences associated with the treatment in a manner to change the state of the blockchain; and
the first event data and the association data are verifiable using the updateable sequence of blocks.

7. A system for tracking events associated with a treatment by personalised medicine, the system comprising:
a plurality of computers and servers hosting a blockchain, the blockchain having:
an associated state storage; and
an updateable sequence of blocks,
wherein the blockchain has a state of the blockchain that is stored on the associated state storage and the updateable sequence of blocks is used in verifying changes to the state of the blockchain,
a plurality of sequence manager nodes each associated with a respective sequence manager contract forming part of the state of the blockchain, each sequence manager contract having associated hub contract storage,
wherein:
the first sequence manager node is arranged to transmit first event data to a first sequence manager contract associated with the first sequence manager node, the first event data indicating a first event associated with the treatment and comparing a timestamp associated with the first event;
the first sequence manager contract is arranged to:
determine whether a difference between the timestamp associated with the first event and a timestamp associated with an earlier event associated with the treatment does not exceed a threshold duration of time; and
in the event that the difference is determined not to exceed the threshold duration of time, store the first event data on the blockchain in association with a first event sequence in a manner to change the state of the blockchain;
the hub contract is arranged to store, in the hub contract storage, association data indicating an association between the first event sequence and one or more further event sequences associated with the treatment in a manner to change the state of the blockchain; and
the first event data and the association data are verifiable using the updateable sequence of blocks.

8. The system of claim 7, wherein
the sequence manager contract is arranged to transmit an alarm message to the hub contract when a difference between a timestamp associated with the first event and a timestamp associated with an earlier event associated with the treatment exceeds a threshold duration of time.

9. A system for tracking events associated with a treatment by personalised medicine, the system comprising:
an automatic temperature sensor for measuring a temperature of physical materials associated with the treatment; and
a plurality of computers and servers hosting a blockchain having:
an associated state storage; and
an updateable sequence of blocks,
wherein the blockchain has a state of the blockchain that is stored on the associated state storage and the updateable sequence of blocks is used in verifying changes to the state of the blockchain,
the plurality of computers and servers comprising:
a plurality of sequence manager nodes each associated with a respective sequence manager contract forming part of the state of the blockchain, each sequence manager contract having associated sequence manager contract storage; and
a hub node associated with a hub contract forming part of the state of the blockchain, the hub contract having associated hub contract storage,
wherein:
the automatic temperature sensor is arranged to transmit the measured temperature of the physical materials to a first sequence manager node of the sequence manager nodes;
the first sequence manager node is arranged to transmit first event data to a first sequence manager contract associated with the first sequence manager node, the first event data indicating a first event associated with the treatment and indicating the measured temperature of the physical materials;
the first sequence manager contract is arranged to:
determine whether the measured temperature lies within a predetermined range; and
in the event that the measured temperature is determined to lie within the predetermined range, store the first event data in the associated sequence manager contract storage in association with a first event sequence in a manner to change the state of the blockchain;
the hub contract is arranged to store, in the hub contract storage, association data indicating an association between the first event sequence and one or more further event sequences associated with the treatment in a manner to change the state of the blockchain; and the first event data and the association data are verifiable using the updateable sequence of blocks.

10. The system of claim 9, wherein the first sequence manager contract is arranged to transmit an alarm message to the hub contract in the event that the first sequence manager contract determines that the measured temperature lies outside the predetermined range.

11. The system of claim 1, wherein the storing of the first event data on the blockchain comprises encrypting the first event data and storing the encrypted first event data on the blockchain.

12. The system of claim 1, wherein the blockchain is a permissioned blockchain.

13. The system of claim 1, wherein the treatment by personalised medicine is a treatment by cell and gene therapy (CGT).

\* \* \* \* \*